US010799094B2

(12) United States Patent
Hiratsuka

(10) Patent No.: US 10,799,094 B2
(45) Date of Patent: Oct. 13, 2020

(54) CONNECTION STRUCTURE FOR WIRE PROTECTIVE SHEATH, CONNECTION MEMBER, WIRE PROTECTIVE SHEATH STRUCTURE, AND CONNECTION METHOD FOR WIRE PROTECTIVE SHEATH

(71) Applicant: OLYMPUS CORPORATION, Hachioji-shi, Tokyo (JP)

(72) Inventor: Yoko Hiratsuka, Kodaira (JP)

(73) Assignee: OLYMPUS CORPORATION, Tokyo (JP)

(*) Notice: Subject to any disclaimer, the term of this patent is extended or adjusted under 35 U.S.C. 154(b) by 979 days.

(21) Appl. No.: 15/373,382

(22) Filed: Dec. 8, 2016

(65) Prior Publication Data
US 2017/0086656 A1 Mar. 30, 2017

Related U.S. Application Data

(63) Continuation of application No. PCT/JP2015/069041, filed on Jul. 1, 2015.

(30) Foreign Application Priority Data

Jul. 7, 2014 (JP) .................. 2014-139761

(51) Int. Cl.
A61B 1/00 (2006.01)
A61B 1/005 (2006.01)
(Continued)

(52) U.S. Cl.
CPC ........ A61B 1/00135 (2013.01); A61B 1/0057 (2013.01); F16G 11/025 (2013.01); F16M 11/10 (2013.01)

(58) Field of Classification Search
CPC ..... A61B 1/0057; F16G 11/025; F16M 11/10; G02B 23/24; G02B 23/2476
See application file for complete search history.

(56) References Cited

U.S. PATENT DOCUMENTS 4,708,137 A * 11/1987 Tsukagoshi ........ A61B 18/1492
606/46
4,841,950 A 6/1989 Fukuda
(Continued)

FOREIGN PATENT DOCUMENTS

JP  58153801 U  10/1983
JP  63111102 U   7/1988
(Continued)

OTHER PUBLICATIONS

International Search Report (ISR) and Written Opinion dated Sep. 29, 2015 issued in International Application No. PCT/JP2015/069041.
(Continued)

Primary Examiner — Daniel J Wiley
(74) Attorney, Agent, or Firm — Holtz, Holtz & Volek PC

(57) ABSTRACT

Provided is a connection structure for connecting a connection member having an attaching portion attachable to an endoscope, to a wire protective sheath into which an endoscope operation wire is configured to be partially inserted for protection. The connection structure includes: a through-hole disposed in the connection member, the wire protective sheath being insertable into the through-hole; and at least one swaging portion located at a different position from that of the attaching portion to partially constitute a peripheral wall of the through-hole. While the wire protective sheath is inserted into the through-hole, the at least one swaging portion is pressed to partially deform the through-hole, thereby connecting the connection member to the wire protective sheath.

18 Claims, 10 Drawing Sheets

(51) Int. Cl.
   *F16M 11/10*   (2006.01)
   *F16G 11/02*   (2006.01)

(56) References Cited

U.S. PATENT DOCUMENTS

| | | | | |
|---|---|---|---|---|
| 5,030,218 | A * | 7/1991 | Alexander | A61B 18/1402 |
| | | | | 606/45 |
| 6,193,717 | B1 * | 2/2001 | Ouchi | A61B 18/1477 |
| | | | | 604/114 |
| 6,402,738 | B1 * | 6/2002 | Ouchi | A61B 10/06 |
| | | | | 600/146 |
| 6,582,450 | B2 * | 6/2003 | Ouchi | A61B 10/06 |
| | | | | 606/205 |
| 8,052,681 | B2 * | 11/2011 | Sugita | A61B 18/1492 |
| | | | | 606/167 |
| 8,100,904 | B2 * | 1/2012 | Sugita | A61B 17/3206 |
| | | | | 606/47 |
| 2006/0178656 | A1 * | 8/2006 | Sugita | G02B 23/2476 |
| | | | | 606/1 |
| 2007/0203487 | A1 * | 8/2007 | Sugita | A61B 18/1492 |
| | | | | 606/45 |
| 2009/0216225 | A1 * | 8/2009 | Ben-Nun | A61B 18/082 |
| | | | | 606/45 |
| 2013/0064530 | A1 * | 3/2013 | Sekido | A61B 1/00124 |
| | | | | 396/17 |
| 2017/0273737 | A1 * | 9/2017 | Iwanami | A61B 18/1482 |

FOREIGN PATENT DOCUMENTS

| | | |
|---|---|---|
| JP | 01104237 A | 4/1989 |
| JP | 02065831 A | 3/1990 |
| JP | 2000225121 A | 8/2000 |
| JP | 2007296189 A | 11/2007 |
| JP | 2012075709 A | 4/2012 |
| JP | 2014000209 A | 1/2014 |

OTHER PUBLICATIONS

Japanese Office Action dated Apr. 24, 2018 issued in counterpart Japanese Application No. 2016-532898.

* cited by examiner

CONNECTION STRUCTURE FOR WIRE PROTECTIVE SHEATH, CONNECTION MEMBER, WIRE PROTECTIVE SHEATH STRUCTURE, AND CONNECTION METHOD FOR WIRE PROTECTIVE SHEATH

CROSS-REFERENCE TO RELATED APPLICATIONS

This application is a continuation of PCT international application Ser. No. PCT/JP2015/069041 filed on Jul. 1, 2015 which designates the United States, incorporated herein by reference, and which claims the benefit of priority from Japanese Patent Application No. 2014-139761, filed on Jul. 7, 2014, incorporated herein by reference.

BACKGROUND

1. Technical Field

The disclosure relates to a connection structure for connecting a wire protective sheath into which an endoscope operation wire is configured to be partially inserted for protection, to a connection member for attaching the wire protective sheath to an operating unit of an endoscope. The disclosure also relates to a connection member used for the connection structure. The disclosure also relates to a wire protective sheath structure in which the wire protective sheath and the connection member are connected, and to a connection method for a wire protective sheath.

2. Related Art

As to an endoscope configured to be inserted into an observation target or a treatment target, a wire disposed in an insertion section is pulled to perform bending operation of a bending section positioned at a distal end of the insertion section. One end of the wire is attached to a bending tube provided on a distal end side of the insertion section, and the other end of the wire is attached to an operating unit provided on a proximal end side of the insertion section. This wire is also called operation wire, or angle wire.

In the insertion section, the wire is protectively disposed in a wire protective sheath having a no pitch coil. One end of the wire protective sheath is fixed to a rear end of the bending tube, and the other end of the wire protective sheath is connected to a cylindrical connection member. The connection member is fixed to a predetermined position of the operating unit.

Repetitive resistance is required for such a connection between the wire protective sheath and the connection member, and soldering has been conventionally used for the connection between the wire protective sheath and the connection member (e.g., see JP 2012-75709 A).

SUMMARY

In some embodiments, provided is a connection structure for connecting a connection member having an attaching portion attachable to an endoscope, to a wire protective sheath into which an endoscope operation wire is configured to be partially inserted for protection. The connection structure includes: a through-hole disposed in the connection member, the wire protective sheath being insertable into the through-hole; and at least one swaging portion located at a different position from that of the attaching portion to partially constitute a peripheral wall of the through-hole. While the wire protective sheath is inserted into the through-hole, the at least one swaging portion is pressed to partially deform the through-hole, thereby connecting the connection member to the wire protective sheath.

In some embodiments, provided is a connection member for disposing, in an operating unit of an endoscope, a wire protective sheath into which an endoscope operation wire is configured to be inserted for protection. The connection member has a cylindrical shape to define a through-hole into which the wire protective sheath is insertable. The connection member includes: an attaching portion provided on a partial area of an outer periphery of the connection member and attachable to the endoscope; and at least one swaging portion located at a different position from that of the attaching portion, partially constituting a peripheral wall of the through-hole, and configured to partially deform the through-hole by application of pressure.

In some embodiments, a wire protective sheath structure includes the connection member; and a wire protective sheath inserted into the through-hole, and connected to the connection member by the at least one swaging portion deformed by application of pressure.

In some embodiments, provided is a method for connecting a connection member having an attaching portion attachable to an endoscope, to a wire protective sheath into which an endoscope operation wire is configured to be partially inserted for protection. The connection member includes a through-hole into which the wire protective sheath is insertable, and at least one swaging portion located at a different position from that of the attaching portion to partially constitute a peripheral wall of the through-hole. The method includes: inserting the wire protective sheath into the through-hole; and pressing the at least one swaging portion to partially deform the through-hole, thereby connecting the wire protective sheath to the connection member.

The above and other features, advantages and technical and industrial significance of this invention will be better understood by reading the following detailed description of presently preferred embodiments of the invention, when considered in connection with the accompanying drawings.

DETAILED DESCRIPTION

Embodiments of a connection structure for a wire protective sheath, a connection member, a wire protective sheath structure, and a connection method for a wire protective sheath according to the present invention will be described in detail with reference to the drawings. The present invention is not limited to these embodiments. The same reference signs are used to designate the same elements throughout the drawings. The drawings are schematically illustrated, and a dimensional relationship or ratio between units may be different from that of actual one. Portions having different dimensional relationships or ratios from each other are included among the drawings.

First Embodiment

Figure 1:
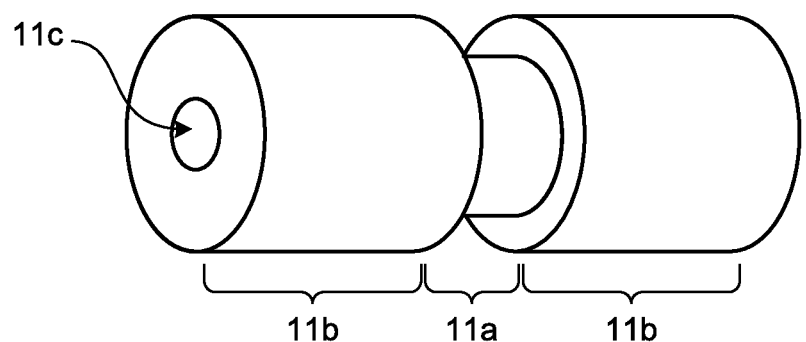
FIG. 1 is an external perspective view of a connection member according to a first embodiment of the present invention.
Figure 2:
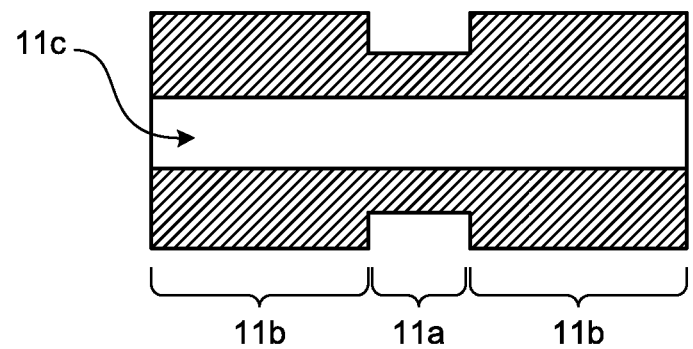
FIG. 2 is a cross-sectional view of the connection member according to the first embodiment of the present invention.

FIG. 1 is an external perspective view of a connection member according to a first embodiment of the present invention. Furthermore, FIG. 2 is a cross-sectional view of a plane including a rotation axis of the connection member according to the first embodiment of the present invention. A connection member 11 according to the first embodiment is a member used for attaching, to an operating unit, a sheath into which an endoscope operation wire is configured to be partially inserted for protection, and has a cylindrical shape having a through-hole 11c provided along the rotation axis, as a whole, as illustrated in FIGS. 1 and 2.

The connection member 11 is made of a metal, and is made of brass in the first embodiment. The connection member 11 has an outer periphery where an attaching portion 11a is provided at a center in a direction in which the through-hole 11c extends, and swaging portions 11b are provided on both sides of the attaching portion 11a. Hereinafter, the direction in which the through-hole 11c extends is referred to as a longitudinal direction.

The attaching portion 11a has a recessed shape having an outer diameter smaller than the outer diameters of the swaging portions 11b. An attaching member, described later, which is fixed to the operating unit of the endoscope is fitted to the attaching portion 11a having the recessed shape, and the connection member 11 is fixed to the operating unit.

The through-hole 11c has an inner diameter large enough to insert therein a wire protective sheath connected to the connection member 11.

Each of the swaging portion 11b partially constitutes a peripheral wall of the through-hole 11c, and is provided at a position different from that of the attaching portion 11a. The swaging portion 11b has a wall thickness peripherally pressed to partially deform the through-hole 11c.

Such a connection member 11 can be fabricated, for example, by forming the through-hole 11c in a columnar member made of brass, and by partially cutting an outer peripheral surface thereof circumferentially to form the attaching portion 11a.

Figure 3:
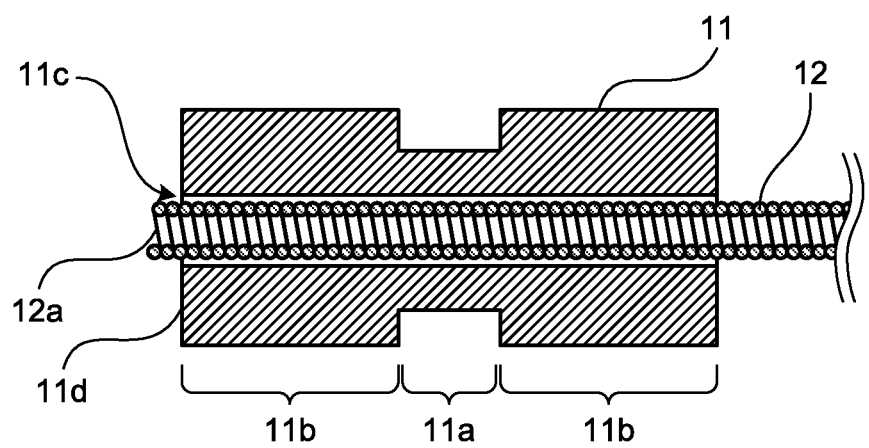
FIG. 3 is a schematic view illustrating a wire protective sheath insertion process in a connection method for a wire protective sheath according to the first embodiment of the present invention.
Figure 4A:
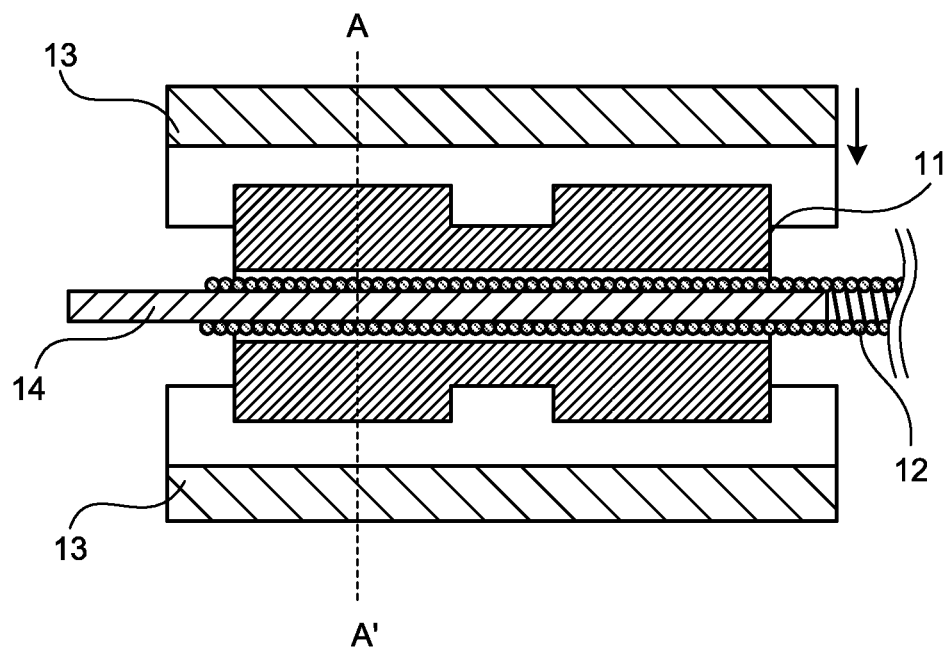
FIG. 4A is a schematic view illustrating a swaging process in the connection method for a wire protective sheath according to the first embodiment of the present invention, and is a cross-sectional view of a state in which the connection member is arranged between a pair of punches of a swaging apparatus, and the cross-sectional view is taken along a longitudinal direction.
Figure 4B:
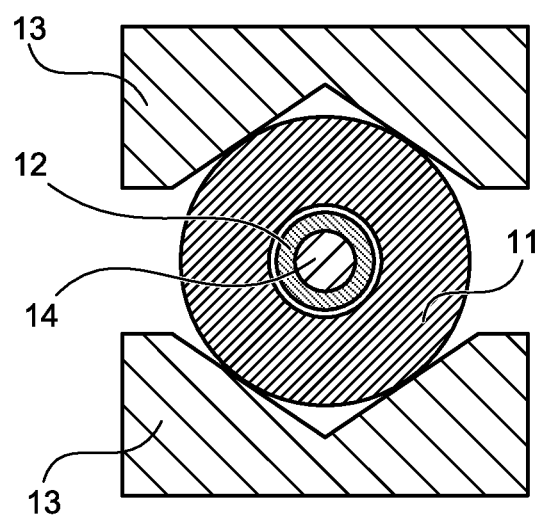
FIG. 4B is a schematic view illustrating the swaging process in the connection method for a wire protective sheath according to the first embodiment of the present invention, and is a cross-sectional view of a plane taken along the line A-A' of FIG. 4A, orthogonal to the longitudinal direction.

Next, a method for connecting the wire protective sheath to the connection member will be described. FIGS. 3, 4A, and 4B are schematic views illustrating a connection method for a wire protective sheath according to the first embodiment. FIG. 3 illustrates a wire protective sheath insertion process, and FIGS. 4A and 4B illustrate a swaging process. As illustrated in FIG. 3, a wire protective sheath 12 has an inner diameter large enough to insert the endoscope operation wire therein, and includes a no pitch coil made of metal such as SUS. In FIG. 3, the wire protective sheath 12 has one end as a right end portion, which is fixed to a bending tube at a distal end of an insertion section of the endoscope.

First, as illustrated in FIG. 3, the wire protective sheath 12 is inserted into the through-hole 11c of the connection member 11. At this time, an end portion 12a of the wire protective sheath 12 is protruded from one end surface 11d of the connection member 11, and the wire protective sheath 12 is fully inserted through the through-hole 11c.

Then, as illustrated in FIGS. 4A and 4B, the connection member 11 through which the wire protective sheath 12 is inserted is arranged in the swaging apparatus to perform swaging. Here, FIG. 4A is a cross-sectional view illustrating a state in which the connection member 11 is arranged between a pair of punches (molds) 13 of the swaging apparatus, and the cross-sectional view is taken along the longitudinal direction, and FIG. 4B is a cross-sectional view of a plane taken along the line A-A' of FIG. 4A, orthogonal to the longitudinal direction.

As illustrated in FIG. 4B, the punches 13 each having a V-shape are used in the first embodiment. When a signal for starting swaging is transmitted to the swaging apparatus to operate the swaging apparatus, one of the punches positioned on the upper side in FIGS. 4A and 4B is moved in a direction approaching the other of the punches, that is, moved downward in FIGS. 4A and 4B. Therefore, a workpiece arranged between the pair of punches 13 is pressed and deformed.

After the connection member 11 is arranged between the pair of punches 13, a mandrel 14 is disposed in an inner diameter portion to prevent reduction in inner diameter of the wire protective sheath 12. When the swaging apparatus is operated to press and deform the swaging portion 11b by the punches 13, in this state, the through-hole 11c positioned inside the swaging portion 11b is also deformed, an inner wall of the through-hole 11c bites into the wire protective sheath 12 in a pressing direction, and the through-hole 11c and the wire protective sheath 12 are firmly fixed to each other. In this way, the connection member 11 and the wire protective sheath 12 are connected to each other. Then, the mandrel 14 is removed.

Figure 5A:
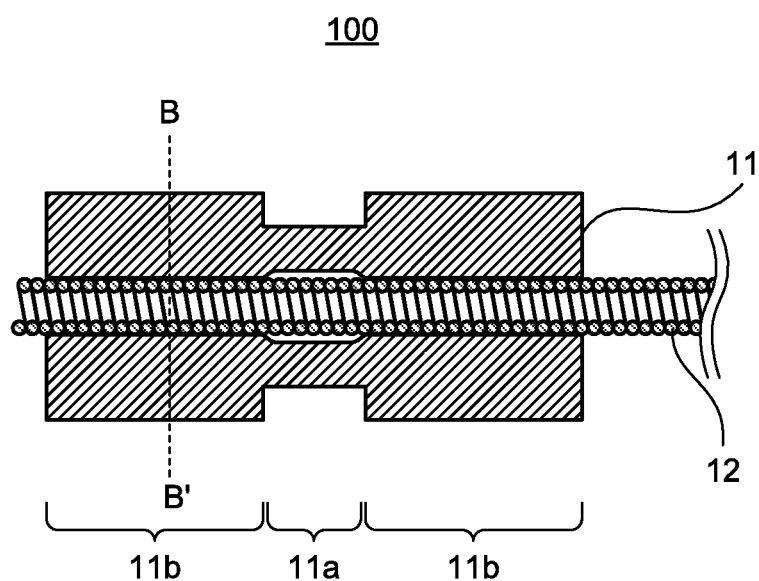
FIG. 5A is a cross-sectional view of a wire protective sheath structure according to the first embodiment of the present invention, which is taken along a longitudinal direction.
Figure 5B:
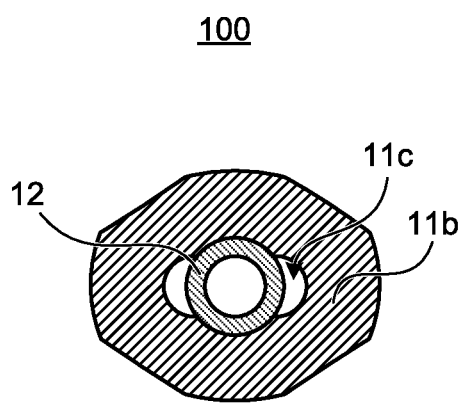
FIG. 5B is a cross-sectional view of a plane taken along the line B-B' of FIG. 5A, orthogonal to the longitudinal direction.

FIGS. 5A and 5B are cross-sectional views illustrating the wire protective sheath structure in which the connection member 11 and the wire protective sheath 12 are connected. FIG. 5A is a cross-sectional view of the wire protective sheath structure 100, which is taken along the longitudinal direction, and FIG. 5B is a cross-sectional view of a plane taken along the line B-B' of FIG. 5A, orthogonal to the longitudinal direction. As illustrated in FIG. 5B, the swaging portion 11b of the connection member 11 is deformed into a substantially rhombic shape in conformance with the shapes of the punches 13 each having the V-shape, and thus, the through-hole 11c is also deformed into a flat shape.

As described above, in the first embodiment, because the connection member 11 and the wire protective sheath 12 are connected not by soldering requiring a high level of skill but by swaging, it is possible to efficiently fabricate the wire protective sheath structure 100 regardless of a worker's skill. Furthermore, since flux causing reduction in corrosion resistance is not used, cleaning of flux is not required, lead time can be reduced, and generation of a failure caused by the reduction in corrosion resistance can be prevented.

Figure 6:
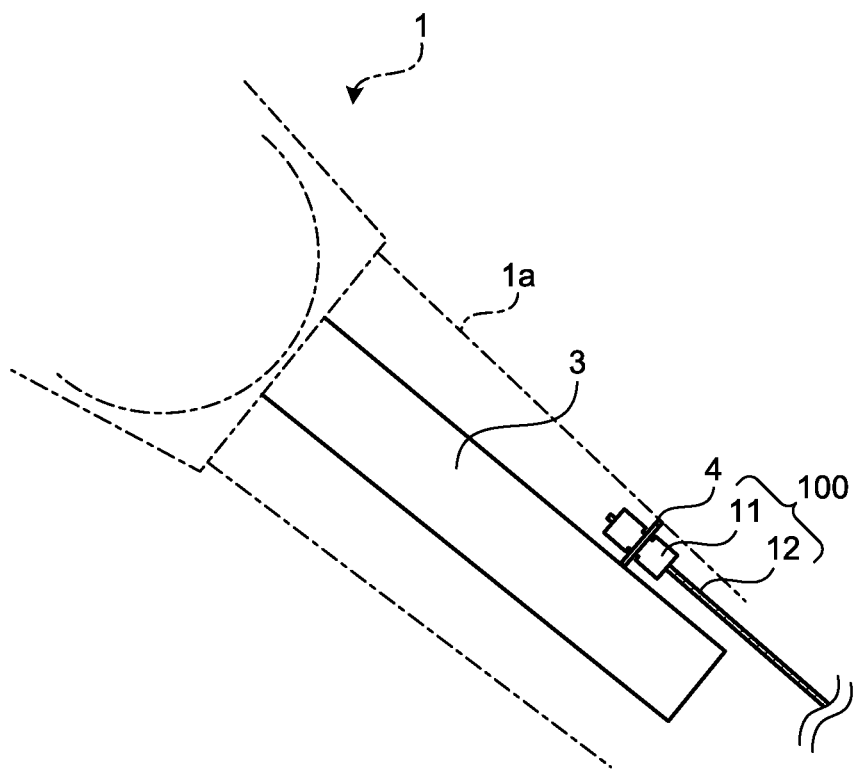
FIG. 6 is a schematic view illustrating a state in which the wire protective sheath structure illustrated in FIGS. 5A and 5B is attached to an operating unit of an endoscope.

FIG. 6 is a schematic view illustrating a state in which the wire protective sheath structure 100 is attached to the operating unit of the endoscope. As illustrated in FIG. 6, inside the operating unit 1, provided is a support portion 3 to which the wire protective sheath structure 100 is configured to be attached. In a space between the support portion 3 and an outer casing 1a of the operating unit 1, an attaching member 4 is fixed.

Figure 7:
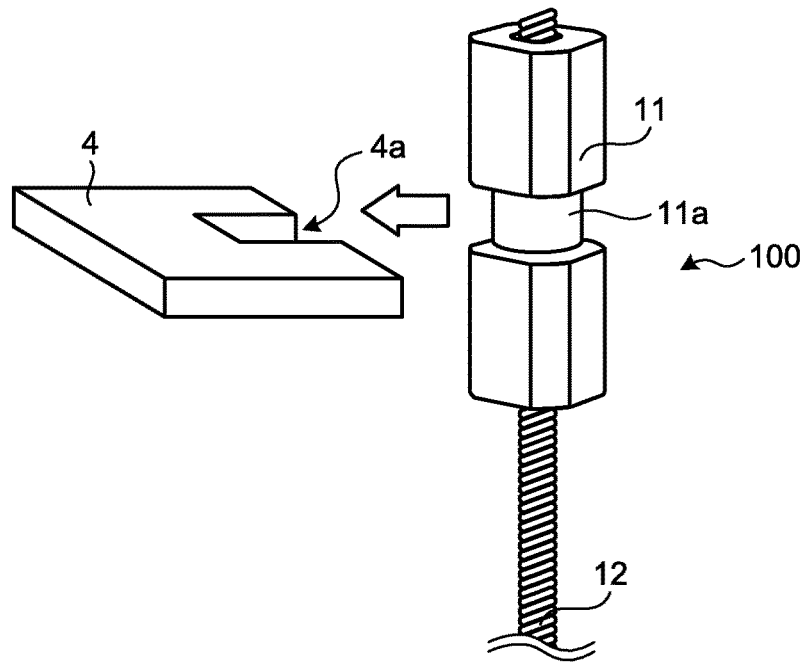
FIG. 7 is a schematic view illustrating a method for attaching the wire protective sheath structure to the operating unit of the endoscope.
Figure 8:
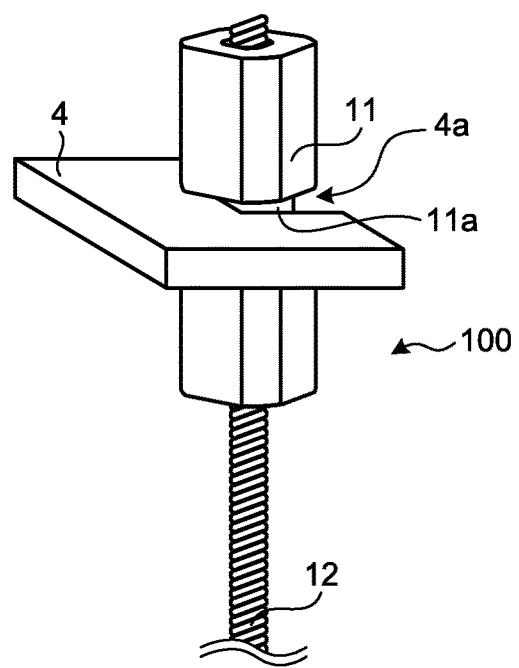
FIG. 8 is a schematic view illustrating the method for attaching the wire protective sheath structure to the operating unit of the endoscope.

FIGS. 7 and 8 are schematic views illustrating a method for attaching the wire protective sheath structure 100 to the operating unit of the endoscope. As illustrated in FIG. 7, the attaching member 4 is a plate-shaped member partially provided with a cutout portion 4a, and is disposed in the operating unit 1 to have a main surface directed orthogonal to a direction in which the wire protective sheath 12 extends (see FIG. 6). The attaching portion 11a of the connection member 11 is fitted into the cutout portion 4a of the attaching member 4, thereby to attach the wire protective sheath structure 100 to the operating unit 1.

As described above, according to the first embodiment of the present invention, the connection member 11 and the wire protective sheath 12 are connected by swaging, and thus, simple operation enables connection between the wire protective sheath 12 and the connection member 11 to have repetitive resistance, without requiring a high level of skill.

In the first embodiment described above, the attaching portion 11a is located at a center of the connection member 11 in a longitudinal direction of the connection member 11, but the location of the attaching portion 11a is not limited to this position. As long as the connection member 11 can be attached to the attaching member 4 of the operating unit 1, the attaching portion 11a may be deviated to one of end portions of the connection member 11, for example.

Furthermore, in the first embodiment described above, the attaching portion 11a of the connection member 11 has a cylindrical shape having the outer diameter smaller than that of the swaging portion 11b, but the shape of the attaching portion 11a is not limited to this shape. As long as the connection member 11 can be attached to the attaching member 4 of the operating unit 1, the attaching portion 11a may have a cylindrical shape having an outer diameter larger than that of the swaging portion 11b, or may have a prism shape having a through-hole, for example.

In the first embodiment described above, the cross-section of the swaging portion 11b after swaging has a substantially rhombic shape, but the cross-section of the swaging portion 11b is not limited to this shape. For example, the cross-section of the swaging portion 11b may have a polygonal shape such as a rectangular or hexagonal shape, or a flat shape formed by merely flattening an original circular shape. When the cross-section of the swaging portion 11b is formed into a shape other than the substantially rhombic shape, swaging may be performed using a punch having a processing surface according to a desired finished shape.

Furthermore, in the first embodiment described above, the swaging portions 11b are provided on both sides of the attaching portions 11a, but only one of the swaging portions 11b may be swaged.

Second Embodiment

Figure 9:
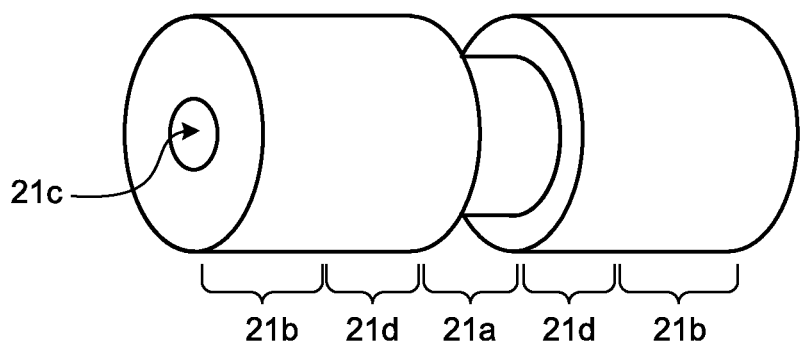
FIG. 9 is an external perspective view of a connection member according to a second embodiment of the present invention.

Next, a second embodiment of the present invention will be described. FIG. 9 is an external perspective view of a connection member according to a second embodiment of the present invention. As illustrated in FIG. 9, a connection member 21 according to the second embodiment has a cylindrical shape, as a whole, in which a through-hole 21c is provided along a rotation axis. A material of the connection member 21 is similar to that in the first embodiment.

The connection member 21 has an outer periphery where an attaching portion 21a is provided at a center in a direction of the through-hole 21c, and swaging portions 21b are provided in both side areas away from the attaching portion 21a, respectively. Hereinafter, an area positioned between the attaching portion 21a and each of the swaging portion 21b is referred to as an intermediate portion 21d. Furthermore, hereinafter, the direction in which the through-hole 21c extends is referred to as a longitudinal direction.

Figure 10:
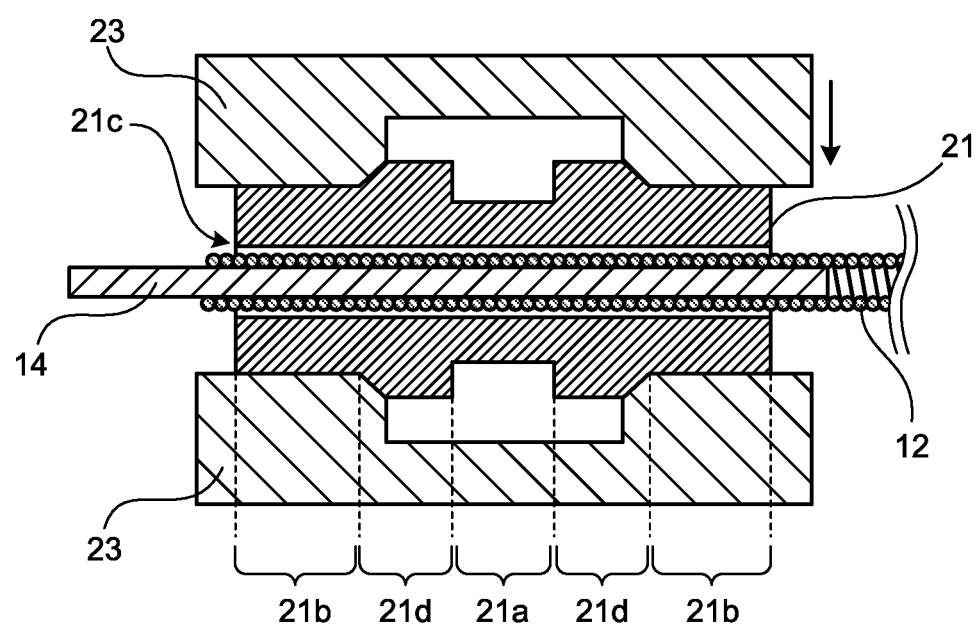
FIG. 10 is a schematic view illustrating a swaging process in a connection method for a wire protective sheath according to the second embodiment of the present invention.

FIG. 10 is a schematic view illustrating a swaging process in a connection method for a wire protective sheath according to the second embodiment of the present invention. The connection method for a wire protective sheath according to the second embodiment is similar to that in the first embodiment as a whole, and is different from the first embodiment in a punch used in the swaging process. As illustrated in FIG. 10, in the second embodiment, a pair of punches 23 is used for pressing only the swaging portions 21b excluding the intermediate portions 21d.

Figure 11:
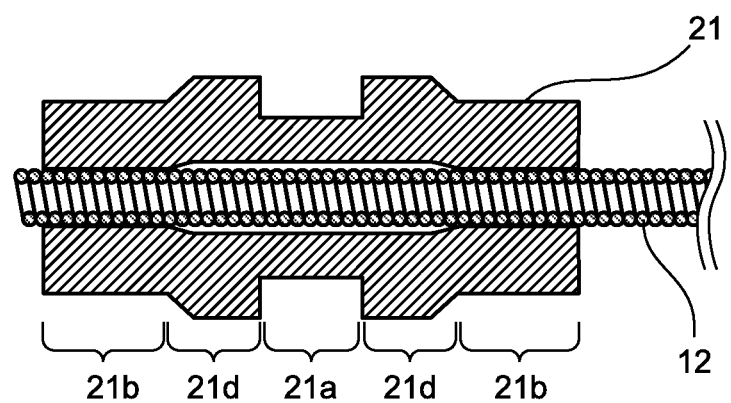
FIG. 11 is a cross-sectional view illustrating a wire protective sheath structure according to the second embodiment of the present invention.

FIG. 11 is a cross-sectional view illustrating a wire protective sheath structure in which the connection member 21 and the wire protective sheath 12 are connected. As illustrated in FIG. 11, in a wire protective sheath structure 200, the swaging portions 21b at both ends of the connection member 21 are deformed by application of pressure, and each of the intermediate portions 21d maintains an original outer diameter.

Here, when a whole area of the outer periphery of the connection member 11, other than the attaching portion 11a, is pressed and deformed to have the swaging portions 11b, as described in the first embodiment, the attaching portion 11a adjacent to the swaging portions 11b is sometimes slightly deformed with the deformation of the swaging portions 11b. In this case, deformation of the attaching portion 11a may cause damage in attaching function, such as rattling, upon attaching the wire protective sheath structure 100 to the attaching member 4 (see FIG. 8).

In contrast, in the second embodiment, since the intermediate portion 21d is provided between the attaching portion 21a and the swaging portion 21b, the attaching portion 21a is prevented from being deformed with the deformation of the swaging portions 21b. Therefore, the wire protective sheath structure 200 can be accurately attached to the attaching member 4 without deteriorating the attaching function of the attaching portion 21a.

Third Embodiment

Figure 12:
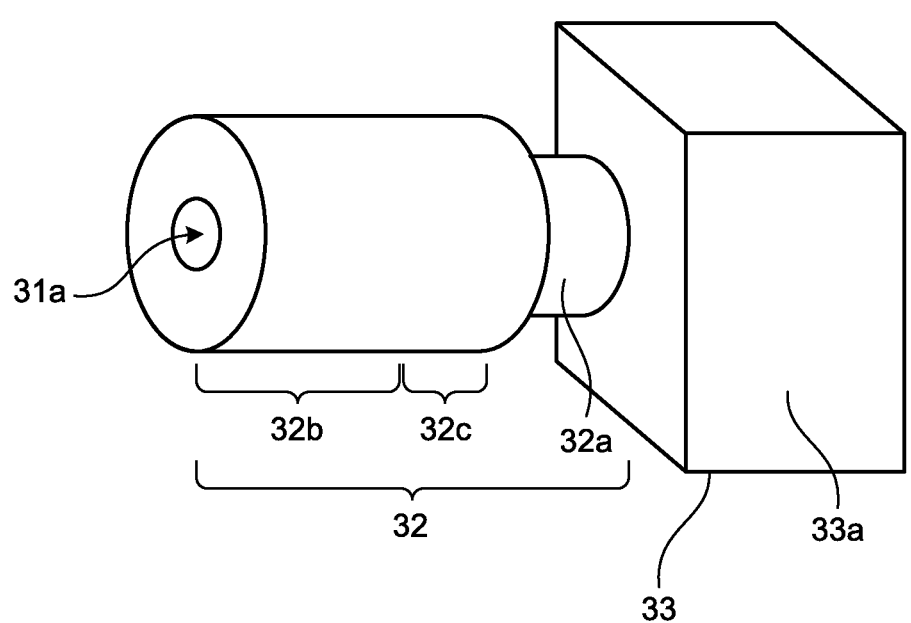
FIG. 12 is an external perspective view of a connection member according to a third embodiment of the present invention.

Next, a third embodiment of the present invention will be described. FIG. 12 is an external perspective view of a connection member according to the third embodiment of the present invention. As illustrated in FIG. 12, a connection member 31 according to the third embodiment includes a cylindrical portion 32 having a cylindrical shape, and a rotation stopper portion 33 positioned on one end surface of the cylindrical portion 32. Furthermore, a through-hole 31a having an inner diameter large enough to insert the wire protective sheath is formed along a center axis of the cylindrical portion 32 and the rotation stopper portion 33. A material of the connection member 31 is similar to that in the first embodiment.

Such a connection member 31 can be fabricated by forming the through-hole 31a in a prismatic member made of brass, and partially cutting an outer peripheral surface of the prismatic member circumferentially to form the cylindrical portion 32, for example.

The cylindrical portion 32 has an outer periphery where an attaching portion 32a is provided in an end area on the rotation stopper portion 33 side, and a swaging portion 32b is provided in an area away from the attaching portion 32a. Hereinafter, an area positioned between the attaching portion 32a and the swaging portion 32b is referred to as an intermediate portion 32c.

The attaching portion 32a has an outer diameter smaller than those of the swaging portion 32b and the intermediate portion 32c, and has a recessed shape between the swaging portion 32b and the intermediate portion 32c, and the rotation stopper portion 33.

The rotation stopper portion 33 has side surfaces parallel to a direction in which the through-hole 31a extends, and at least part of the side surfaces is flat. In the third embodiment, the rotation stopper portion 33 has an outer periphery of prism shape, and all of the side surfaces parallel to the direction in which the through-hole 31a extends is flat. One of the flat side surfaces, for example, a side surface 33a, serves as an anti-rotation surface for preventing rotation of the connection member 31 upon attaching the connection member 31 to the operating unit of the endoscope.

A distance from a rotation axis of the through-hole 31a to the anti-rotation surface, that is, to the side surface 33a is equal to or larger than a distance from the rotation axis to a portion of the cylindrical portion 32 projecting farthest, that is, to the intermediate portion 32c.

Figure 13:
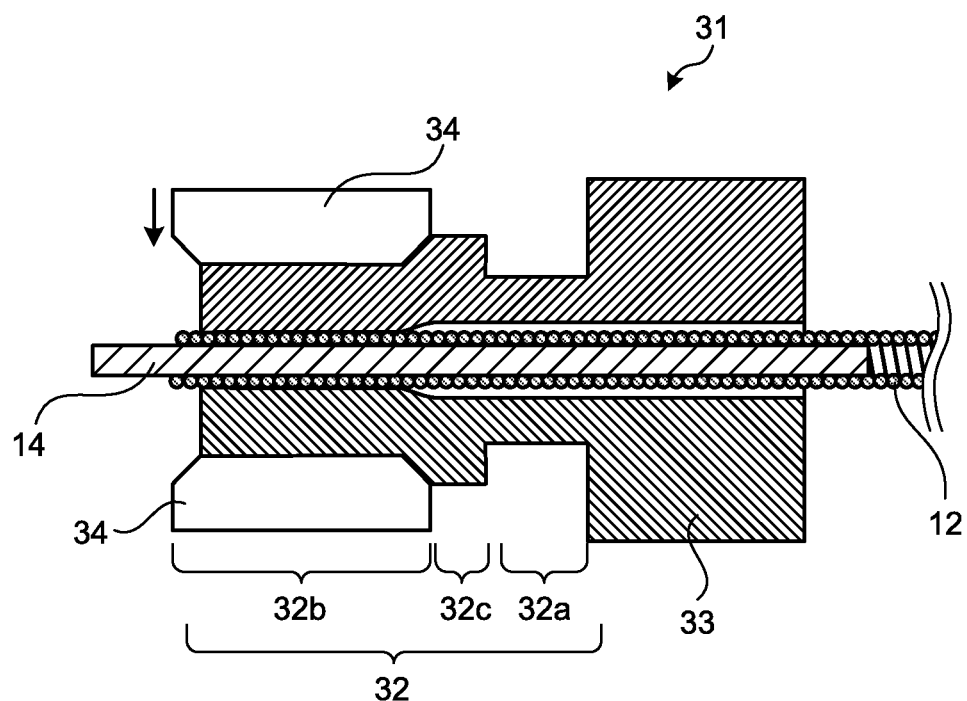
FIG. 13 is a schematic view illustrating a swaging process in a connection method for a wire protective sheath according to the third embodiment of the present invention.

FIG. 13 is a schematic view illustrating a swaging process in a connection method for a wire protective sheath according to the third embodiment. The connection method for a wire protective sheath according to the third embodiment is similar to that in the first embodiment as a whole, and is different from the first embodiment in a punch used in the swaging process. As illustrated in FIG. 13, in the third embodiment, a pair of punches 34 is used to press only the swaging portion 32b provided at one end portion of the cylindrical portion 32 excluding the intermediate portion 32c.

Figure 14:
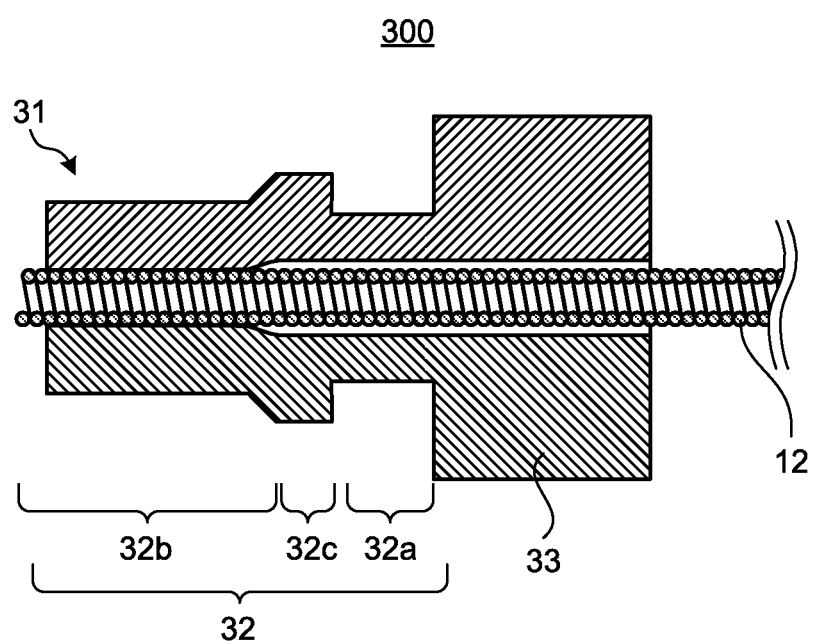
FIG. 14 is a cross-sectional view illustrating a wire protective sheath structure according to the third embodiment of the present invention.

FIG. 14 is a cross-sectional view illustrating a wire protective sheath structure in which the connection member 31 and the wire protective sheath 12 are connected. As illustrated in FIG. 14, in a wire protective sheath structure 300, the swaging portion 32b at one end side of the connection member 31 is deformed by application of pressure, and the intermediate portion 32c, the attaching portion 32a, and the rotation stopper portion 33 maintain original sizes thereof.

Figure 15:
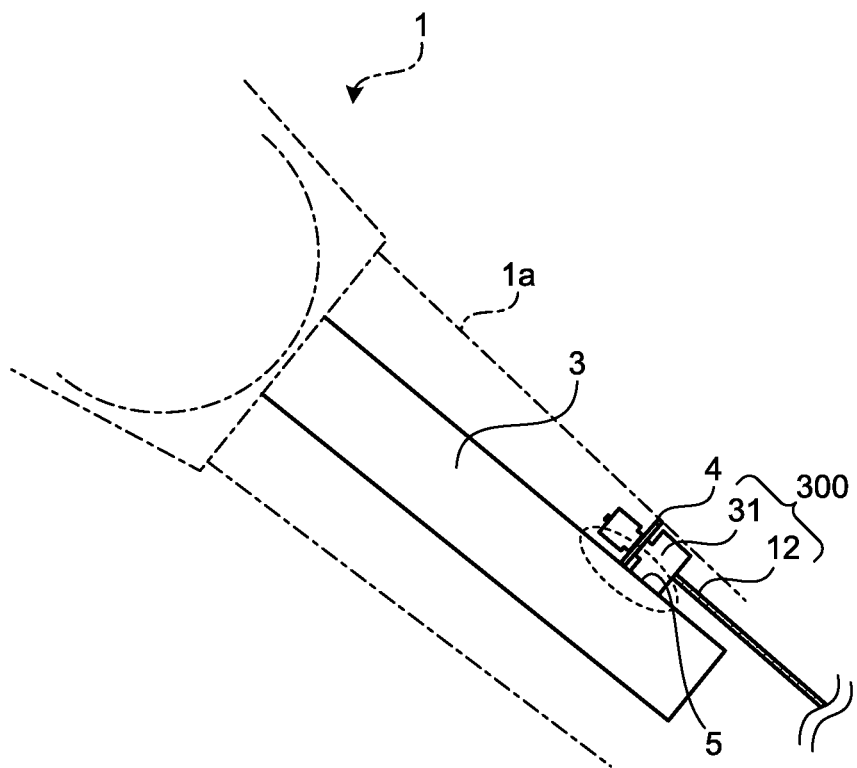
FIG. 15 is a schematic view illustrating a state in which the wire protective sheath structure illustrated in FIG. 14 is attached to the operating unit of the endoscope.

FIG. 15 is a schematic view illustrating a state in which the wire protective sheath structure 300 is attached to the operating unit of the endoscope. As illustrated in FIG. 15, inside the operating unit 1, provided is a support portion 3 to which the wire protective sheath structure 300 is configured to be attached. In a space between the support portion 3 and the outer casing 1a of the operating unit 1, the attaching member 4 is fixed.

When the wire protective sheath structure 300 is attached to the operating unit 1, the attaching portion 32a of the connection member 31 is fitted to the cutout portion 4a of the attaching member 4 (see FIG. 8), and the anti-rotation surface of the rotation stopper portion 33, for example the side surface 33a is brought into contact with a wall surface 5 of the support portion 3. Therefore, rotation of the wire protective sheath structure 300 about the rotation axis can be prevented.

As described above, according to the third embodiment of the present invention, since the intermediate portion 32c is provided between the attaching portion 32a and the swaging portion 32b, the attaching portion 32a can be prevented from being deformed with the deformation of the swaging portions 32b. Thus, the connection member 31 can be accurately attached to the attaching member 4 without deteriorating the attaching function of the attaching portion 32a.

Furthermore, according to the third embodiment of the present invention, the connection member 31 includes the rotation stopper portion 33 having at least part of the side surfaces being flat. With this structure, when the wire protective sheath structure 300 is attached to the attaching member 4, rotation of the connection member 31 can be prevented. Therefore, damage caused by distortion of the wire protective sheath 12 can be inhibited.

Furthermore, according to the third embodiment of the present invention, the intermediate portion 32c and the attaching portion 32a are interposed between the swaging portion 32b and the rotation stopper portion 33, and thus, the rotation stopper portion 33 can be prevented from being deformed with the deformation of the swaging portion 32b during swaging. Accordingly, rotation preventing function of the rotation stopper portion 33 can be accurately exhibited.

The present invention described above is not limited to the first to third embodiments, and a plurality of elements disclosed in the embodiments can be appropriately combined to form various inventions. For example, the inventions may be made by eliminating some of all elements in each embodiment or by appropriately combining elements in different embodiments.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A connection structure for an endoscope, the connection structure comprising:

a connection member including an attaching portion that is attachable to the endoscope, a through-hole, and at least one swaging portion located at a different position than the attaching portion along a direction in which the through-hole extends, the at least one swaging portion partially constituting a peripheral wall of the through-hole; and a wire protective sheath configured to have an endoscope operation wire partially inserted therein for protection, the wire protective sheath being inserted into the through-hole of the connection member, wherein the at least one swaging portion has a structure formed by, while the wire protective sheath is inserted into the through-hole, pressing the at least one swaging portion in a direction crossing the direction in which the through-hole extends to partially plastically deform the through-hole in a radial direction and make the through-hole contact an outer peripheral surface of the wire protective sheath, thereby connecting the connection member to the wire protective sheath.

2. The connection structure according to claim 1, wherein the connection member further includes at least one intermediate portion located between the at least one swaging portion and the attaching portion along the direction in which the through-hole extends.

3. The connection structure according to claim 2, wherein in the connection member, an outer diameter of the attaching portion is smaller than an outer diameter of the at least one swaging portion, and wherein an outer diameter of the at least one intermediate portion is greater than the outer diameter of the at least one swaging portion.

4. The connection structure according to claim 1, wherein in the connection member, an outer diameter of the attaching portion is smaller than an outer diameter of the at least one swaging portion.

5. The connection structure according to claim 1, wherein the at least one swaging portion is two swaging portions, and the attaching portion is located between the two swaging portions along the direction in which the through-hole extends.

6. The connection structure according to claim 5, wherein the connection member further includes two intermediate portions which are respectively located between the two swaging portions and the attaching portion along the direction in which the through-hole extends.

7. The connection structure according to claim 1, wherein the connection member further comprises a rotation stopper portion located at a different position than the at least one swaging portion and the attaching portion, the rotation stopper portion having side surfaces parallel to the direction in which the through-hole extends, and at least part of the side surfaces being flat.

8. A connection member configured to be disposed in an operating unit of an endoscope, the connection member comprising:

a cylindrical portion including a through-hole;

an attaching portion provided on a part of an outer periphery of the cylindrical portion and attachable to the endoscope; and at least one swaging portion located on the cylindrical portion at a different position than the attaching portion along a direction in which the through-hole extends, wherein the at least one swaging portion partially constitutes a peripheral wall of the through-hole and is configured to partially plastically deform the through-hole in a radial direction by application of pressure on the at least one swaging portion in a direction crossing the direction in which the through-hole extends, and wherein the through-hole of the cylindrical portion has an inner diameter with a size that enables insertion, into the through-hole, of a wire protective sheath into which an endoscope operation wire is configured to be inserted for protection.

9. The connection member according to claim 8, wherein the connection member further includes at least one intermediate portion located between the at least one swaging portion and the attaching portion along the direction in which the through-hole extends.

10. The connection member according to claim 8, further comprising a rotation stopper portion located at an end of the cylindrical portion and at a different position than the at least one swaging portion and the attaching portion, the rotation stopper portion having side surfaces parallel to the direction in which the through-hole extends, and at least part of the side surfaces being flat.

11. A wire protective sheath structure comprising:

the connection member according to claim 8; and the wire protective sheath, which is inserted into the through-hole and is connected to the connection member by the at least one swaging portion deformed by application of pressure to plastically deform the through-hole in the radial direction and make the through-hole contact an outer peripheral surface of the wire protective sheath.

12. The connection member according to claim 8, wherein an outer diameter of the attaching portion is smaller than an outer diameter of the at least one swaging portion.

13. The connection member according to claim 8, wherein the at least one swaging portion is two swaging portions, and the attaching portion is located between the two swaging portions along the direction in which the through-hole extends.

14. The connection member according to claim 13, further comprising two intermediate portions which are respectively located between the two swaging portions and the attaching portion along the direction in which the through-hole extends.

15. A method for connecting a connection member to a wire protective sheath configured to have endoscope operation wire partially inserted therein for protection, the connection member comprising an attaching portion which is attachable to an endoscope, a through-hole into which the wire protective sheath is insertable, and at least one swaging portion located at a different position than the attaching portion along a direction in which the through-hole extends, the at least one swaging portion partially constituting a peripheral wall of the through-hole, the method comprising:

inserting the wire protective sheath into the through-hole; and pressing, in a direction crossing the direction in which the through-hole extends, the at least one swaging portion to partially plastically deform the through-hole in a radial direction and make the through-hole contact an outer peripheral surface of the wire protective sheath, thereby connecting the wire protective sheath to the connection member.

16. The method according to claim 15, wherein in the connection member, an outer diameter of the attaching portion is smaller than an outer diameter of the at least one swaging portion, and wherein the outer diameter of the attaching portion is maintained when the at least one swaging portion is pressed to partially plastically deform the through-hole.

17. The method according to claim 16, wherein the connection member further comprises at least one intermediate portion located between the at least one swaging portion and the attaching portion along the direction in which the through-hole extends, wherein an outer diameter of the at least one intermediate portion is greater than the outer diameter of the at least one swaging portion, and wherein the outer diameter of the at least one intermediate portion is maintained when the at least one swaging portion is pressed to partially plastically deform the through-hole.

18. The method according to claim 15, wherein the connection member further comprises a rotation stopper portion located at a different position than the at least one swaging portion and the attaching portion, the rotation stopper portion having side surfaces parallel to the direction in which the through-hole extends, and at least part of the side surfaces being flat, and wherein an outer diameter of the rotation stopper portion is maintained when the at least one swaging portion is pressed to partially plastically deform the through-hole.

* * * * *